United States Patent
Matsuura et al.

(10) Patent No.: US 11,866,403 B2
(45) Date of Patent: Jan. 9, 2024

(54) CARBOXYLIC ACID ESTER COMPOUND, METHOD FOR PRODUCING THE SAME, COMPOSITION, AND, FRAGRANCE COMPOSITION

(71) Applicant: Mitsubishi Gas Chemical Company, Inc., Chiyoda-ku (JP)

(72) Inventors: Yutaka Matsuura, Niigata (JP); Tomohiko Hakamata, Yokohama (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 549 days.

(21) Appl. No.: 17/259,424

(22) PCT Filed: May 28, 2019

(86) PCT No.: PCT/JP2019/021171
§ 371 (c)(1),
(2) Date: Jan. 11, 2021

(87) PCT Pub. No.: WO2020/012806
PCT Pub. Date: Jan. 16, 2020

(65) Prior Publication Data
US 2021/0276941 A1    Sep. 9, 2021

(30) Foreign Application Priority Data
Jul. 13, 2018    (JP) .................................. 2018-132789

(51) Int. Cl.
*C07C 69/753* (2006.01)
*C11B 9/00* (2006.01)

(52) U.S. Cl.
CPC .......... *C07C 69/753* (2013.01); *C11B 9/0049* (2013.01); *C07C 2601/04* (2017.05); *C07C 2602/44* (2017.05)

(58) Field of Classification Search
CPC ... C07C 67/38; C07C 69/753; C07C 2601/04; C07C 2602/44; C11B 9/0049
USPC ............................................. 512/16, 14, 8, 1
See application file for complete search history.

(56) References Cited

U.S. PATENT DOCUMENTS

2014/0087990 A1    3/2014  Kitamura

FOREIGN PATENT DOCUMENTS

WO    WO 2012/063433 A1    5/2012
WO    WO 2012/133189 A1    10/2012

OTHER PUBLICATIONS

Goulet et al, Non-Amines, Drugs Without an Amine Nitrogen, Potently Block Serotonin Transport: Novel Antidepressant Candidates?,2001, Synapse, 42, 129-140 (Year: 2001).*
Goulet, M. et al., "Non-amines, Drugs Without an Amine Nitrogen, Potently Block Serotonin Transport: Novel Antidepressant Candidates?" Synapse, vol. 42, 2001, pp. 129-140.
Xie, W. et al., "Structure-Activity Relationship of Aza-Steroids as PI-PLC Inhibitors," Bioorganic & Medicinal Chemistry, vol. 9, 2001, pp. 1073-1083.
Nakajima, M., "Koryo to Chokok No Kiso Chishiki (Basic Knowledge of Fragrances and Fragrance Preparation," 1995, p. 215, p. 235, p. 244-247, 8 total pages, Sangyo Tosho).
International Search Report dated Aug. 6, 2019 in PCT/JP2019/021171 filed on May 28, 2019, 1 page.

* cited by examiner

*Primary Examiner* — Jessica Whiteley
(74) *Attorney, Agent, or Firm* — Oblon, McClelland, Maier & Neustadt, L.L.P.

(57) ABSTRACT

The present invention provides a carboxylic acid ester compound represented by formula (1) that is useful as a fragrance component or as a formulated fragrance material,

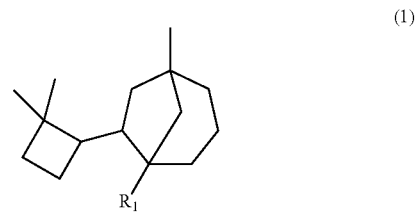

(1)

wherein $R^1$ is —COOR, wherein R is an alkyl group having 1 to 4 carbon atoms.

5 Claims, 1 Drawing Sheet

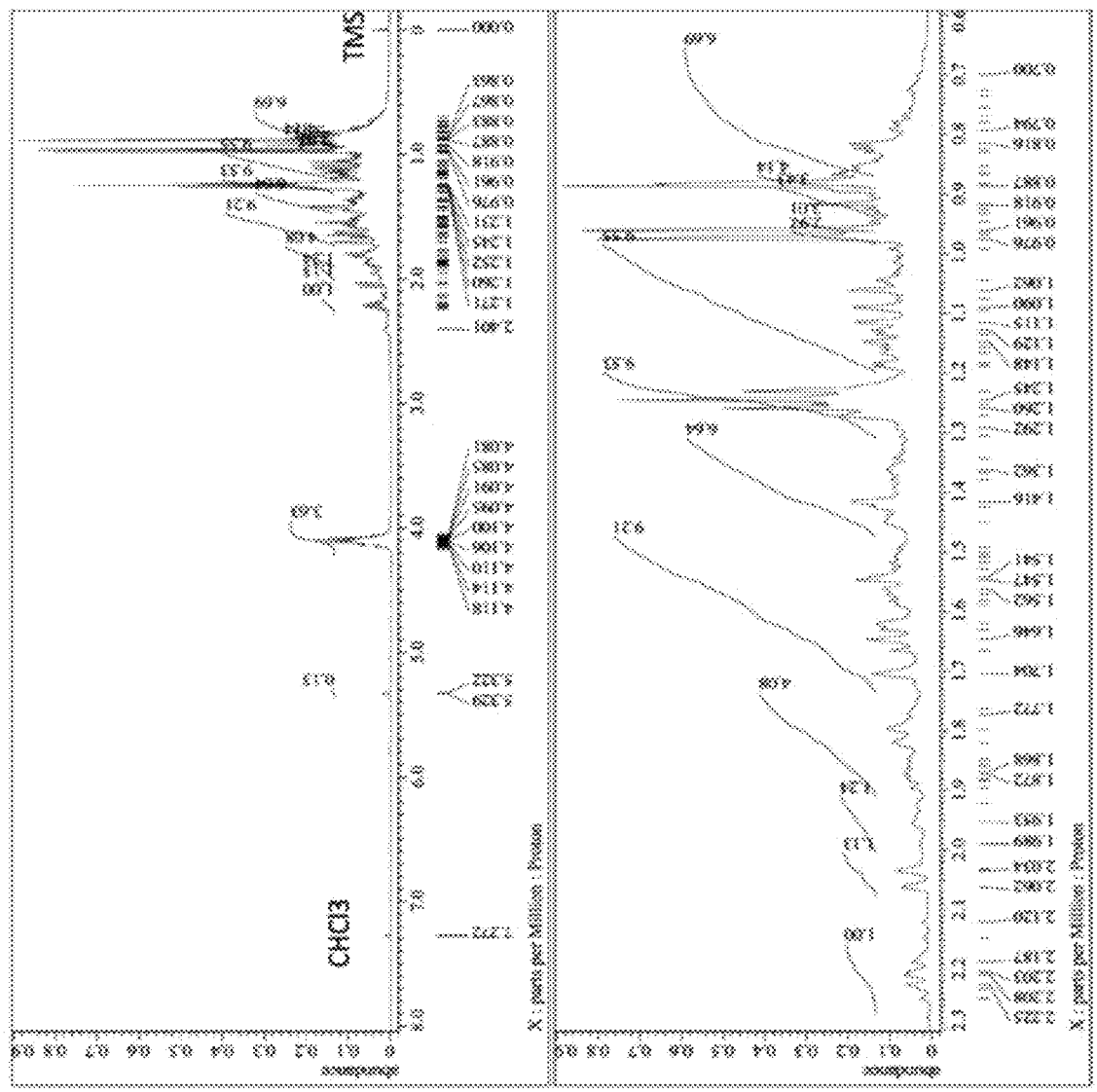

CARBOXYLIC ACID ESTER COMPOUND, METHOD FOR PRODUCING THE SAME, COMPOSITION, AND, FRAGRANCE COMPOSITION

TECHNICAL FIELD

The present invention relates to a carboxylic acid ester compound, a method for producing the same, a composition, and a fragrance composition. The present invention more particularly relates to a carboxylic acid ester of a 7-(2,2-dimethylcyclobutyl)-5-methylbicyclo[3.2.1]octane compound.

BACKGROUND ART

It is known that esters include compounds useful as fragrances. For example, in Non Patent Literature 1, it is described that acetate geranyl having a rose-like aroma, methyl jasmonate having a jasmine-like sweet aroma, FRUITATE having a fruity note, methyl benzoate having a strong dry fruity note, and the like are useful as formulated fragrance materials.

CITATION LIST

Non Patent Literature

Non Patent Literature 1: Motoki Nakajima ed., "Koryo To Choko No Kiso Chishiki (Basic Knowledge of Fragrances and Fragrance Preparation", 1995, p. 215, p. 235, pp. 244 to 247, Sangyo Tosho)

SUMMARY OF INVENTION

Technical Problem

In recent years, the preferences of consumers have been diversified, and the demands have also extended to the scent of products. In order to address such diversity, the development of unprecedented fragrance components has been demanded.

The present invention has been made in order to solve such a problem, and it is an object of the present invention to provide a compound useful as a fragrance component or as a formulated fragrance material, and a method for producing the same, and a composition and a fragrance composition containing the carboxylic acid ester compound.

Solution to Problem

The present inventors have studied diligently in order to solve such a problem, and synthesized various compounds and evaluated their properties, and as a result found that a carboxylic acid ester compound represented by formula (1) is useful as a fragrance component or as a formulated fragrance material, and completed the present invention.

Specifically, the present invention is as follows.

[1]
A carboxylic acid ester compound represented by formula (1),

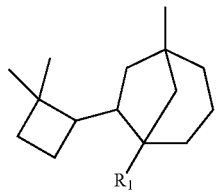

(1)

wherein $R^1$ is —COOR, wherein R is an alkyl group having 1 to 4 carbon atoms.

[2]
A fragrance composition comprising the carboxylic acid ester compound according to [1].

[3]
A composition comprising the carboxylic acid ester compound according to [1].

[4]
The composition according to [3], for use in cosmetics, food additives, or cleaning compositions.

[5]
A method for producing a carboxylic acid ester compound represented by formula (1), comprising a step of reacting β-caryophyllene represented by formula (2) with carbon monoxide and then a monohydric alcohol having 1 to 4 carbon atoms in the presence of hydrogen fluoride,

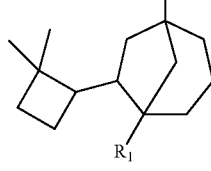

(2)

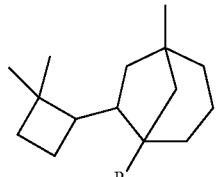

(1)

wherein $R^1$ is —COOR, wherein R is an alkyl group having 1 to 4 carbon atoms.

Advantageous Effects of Invention

According to the present invention, a carboxylic acid ester compound is provided, and such a carboxylic acid ester compound is useful as a fragrance component or as a formulated fragrance material. By using such a carboxylic acid ester compound as a perfuming component or a formulation and fragrance preparation material, the diversification of scents can be promoted in a wide range of products, for example, cosmetics, health and sanitary materials, daily necessities, sundry articles, fibers, fiber products, clothing, food, quasi-drugs, and medicaments.

BRIEF DESCRIPTION OF DRAWING

FIG. 1 shows diagrams showing the $^1$H-NMR spectrum data of 7-(2,2-dimethylcyclobutyl)-5-methylbicyclo[3.2.1] octane-1-carboxylic acid ethyl ester. An overall view is shown for the spectrum data in the upper row, and an enlarged view at 2.3 ppm to 0.6 ppm is shown for the spectrum data in the lower row.

DESCRIPTION OF EMBODIMENTS

Embodiments of the present invention will be described below. The embodiments below are illustrations for describing the present invention, and the present invention is not limited to only the embodiments. As used herein, when an expression is given by using "to" and inserting numerical values or physical property values before and after "to", the expression is used as including the values before and after "to". For example, the description of a numerical value range as "1 to 100" includes both the upper limit value "100" and the lower limit value "1". The same applies to the description of other numerical value ranges.

[Compound]

The compound of this embodiment is a carboxylic acid ester compound represented by formula (1). The compound of this embodiment has a fruity, apple-like aroma with a clean feeling, has a high preference, has excellent aroma properties, and is useful as a fragrance component or as a formulated fragrance material, as described in Examples described later.

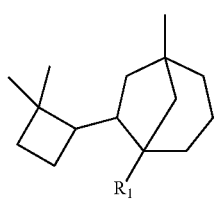

(1)

wherein $R^1$ is —COOR, wherein R is an alkyl group having 1 to 4 carbon atoms.

Examples of the alkyl group having 1 to 4 carbon atoms in formula (1) include linear alkyl groups and branched alkyl groups.

Specific examples of the above alkyl group having 1 to 4 carbon atoms include, but are not particularly limited to, a methyl group, an ethyl group, a n-propyl group, an iso-propyl group, a n-butyl group, an iso-butyl group, and a tert-butyl group. Among these, R is preferably an ethyl group.

As the carboxylic acid ester compound represented by formula (1), several types of isomers can be present, and the carboxylic acid ester compound represented by formula (1) may be any single one of the isomers, or a mixture in which these are contained in any proportion. Specific examples of the isomers include optical isomers and structural isomers.

[Method for Producing Carboxylic Acid Ester Compound]

The carboxylic acid ester compound of this embodiment can be produced by reacting β-caryophyllene represented by formula (2) with carbon monoxide and then a monohydric alcohol having 1 to 4 carbon atoms in the presence of hydrogen fluoride (hereinafter also simply described as "HF"). The carboxylic acid ester compound represented by formula (1) is specifically synthesized based on the following reaction path. Synthesizing the carboxylic acid ester compound represented by formula (1) based on the following reaction path is industrially advantageous, and the economy and the productivity are increased.

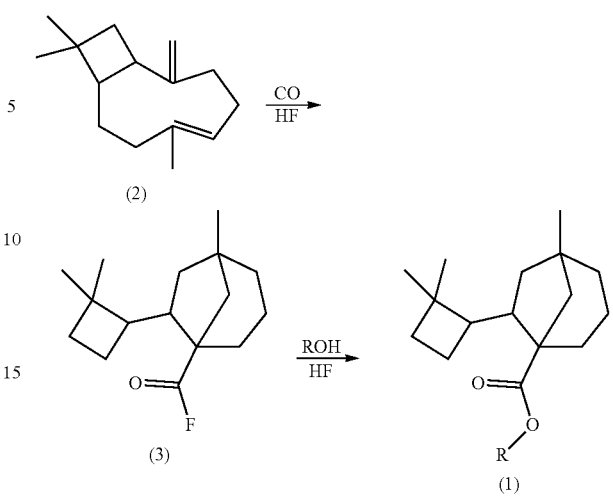

A preferred production method of this embodiment will be described in detail below.

The method for producing a carboxylic acid ester compound represented by formula (1) in this embodiment comprises the step of a first-stage reaction in which a compound represented by formula (2) is used as a starting raw material, and this is reacted with carbon monoxide in the presence of HF to obtain an acyl fluoride of a 7-(2,2-dimethylcyclobutyl)-5-methylbicyclo[3.2.1]octane compound represented by formula (3) mainly by the skeletal isomerization and carbonylation of the above compound represented by formula (2) (the first-stage reaction is hereinafter also simply referred to as a "carbonylation reaction"), and the step of a second-stage reaction in which the obtained acyl fluoride of formula (3) is reacted with an alcohol for esterification (the second-stage reaction is hereinafter also simply referred to as an "esterification reaction").

(Compound Represented by Formula (2))

The compound represented by formula (2) is β-caryophyllene, and commercial β-caryophyllene can be used. The compound represented by formula (2) may be any single one of the isomers, or a mixture in which these are contained in any proportion. Here, specific examples of the isomers include optical isomers and structural isomers.

(HF)

The HF used in the carbonylation reaction functions as a solvent and a catalyst and is also a secondary raw material in the carbonylation reaction, and therefore is preferably a substantially anhydrous substance, that is, anhydrous hydrogen fluoride (also referred to as anhydrous hydrofluoric acid and hereinafter also described as anhydrous HF). The amount of HF used can be appropriately set as needed and is not particularly limited but is preferably 3 to 25 times by mole, more preferably 8 to 15 times by mole, based on the compound represented by formula (2), which is the main raw material. By setting the molar ratio of HF at 3 times by mole or more and 25 times by mole or less, the carbonylation reaction proceeds efficiently, side reactions such as disproportionation and/or polymerization are suppressed, and the carbonyl compound, which is the target, tends to be obtained in high yield.

(Carbon Monoxide)

As the carbon monoxide used in the carbonylation reaction, known carbon monoxide gas distributed as a general industrial gas can be appropriately used, and the carbon monoxide is not particularly limited. An inert gas and the like such as nitrogen and/or methane may be contained in the carbon monoxide gas.

The above-described carbonylation reaction is preferably carried out in the carbon monoxide partial pressure range of 0.5 to 5.0 MPa, more preferably 1.0 to 3.0 MPa. By setting the carbon monoxide partial pressure at 0.5 MPa or more, the carbonylation reaction proceeds sufficiently, side reactions such as disproportionation and/or polymerization are suppressed, and the alicyclic carbonyl compound, which is the target, tends to be obtained in high yield. By setting the carbon monoxide partial pressure at 5.0 MPa or less, the load on the reaction system (apparatus) tends to be reduced.

(Solvent)

In the above carbonylation reaction, a solvent that dissolves the raw materials and is inert to HF may be used. Such a solvent is not particularly limited, and examples thereof include saturated hydrocarbon compounds such as hexane, heptane, and decane.

Whether the solvent is used or not, and the amount of the solvent used should be appropriately set considering other reaction conditions, and are not particularly limited, but the amount of the solvent used is preferably 0.2 to 2.0 times by mass based on the compound represented by formula (2), which is the main raw material, from the viewpoint of suppressing polymerization reactions to increase the yield, and preferably 0.5 to 1.0 times by mass from the viewpoint of productivity and energy efficiency.

(Alcohol)

In the above carbonylation reaction, an alcohol may be used. By adding an alcohol as an esterifying agent during the carbonylation reaction step, side reactions tends to be able to be suppressed in the carbonylation reaction. Here, examples of alcohols that can be used include methanol, ethanol, n-propanol, iso-propanol, n-butanol, iso-butanol, and tert-butanol.

Whether an alcohol is used or not, and the amount of the alcohol used, in the carbonylation reaction should be appropriately set considering other reaction conditions, and are not particularly limited, but the amount of the alcohol used is preferably 0.1 to 0.9 times by mole, more preferably 0.2 to 0.9 times by mole, based on the compound represented by formula (2), which is the main raw material. By setting the amount of the alcohol used in the range of 0.1 to 0.9 times by mole, the carbonylation reaction proceeds sufficiently, side reactions such as disproportionation and/or polymerization are suppressed, and the alicyclic carbonyl compound (acyl fluoride), which is the target in this step, tends to be obtained in high yield.

(Carbonylation Reaction Conditions)

The reaction temperature in the above carbonylation reaction is not particularly limited but is preferably −30° C. to 30° C., more preferably −20° C. to 20° C., from the viewpoint of increasing the reaction rate, and suppressing side reactions to increase the yield, and further obtaining the target having high purity. The reaction time is not particularly limited but is preferably 1 to 5 h from the viewpoint of allowing the carbonylation reaction to proceed sufficiently and increasing the efficiency. Here, the carbonylation reaction is preferably performed under pressurization from the viewpoint of increasing the reaction efficiency. From the viewpoint of increasing the reaction efficiency and reducing the facility burden, the pressure of the carbonylation reaction is preferably 1.0 to 5.0 MPa, more preferably 1.0 to 3.0 MPa. The form of the carbonylation reaction is not particularly limited and may be any method, for example, a batch type, a semicontinuous type, or a continuous type. The end point of the reaction is not particularly limited but should be determined with reference to the point in time when no absorption of carbon monoxide is noted.

A mixed solution (carbonylation reaction-produced liquid) containing, in addition to the acyl fluoride represented by formula (3), which is the reaction product (intermediate), HF, and a solvent, an alcohol, and the like as needed is obtained by the above-described carbonylation reaction.

Then, by reacting the produced alicyclic carbonyl compound (acyl fluoride) represented by formula (3) with an alcohol in the presence of HF, the carboxylic acid ester represented by formula (1) is obtained. This esterification reaction can be carried out by once separating and purifying the produced acyl fluoride represented by formula (3) from the above carbonylation reaction-produced liquid according to an ordinary method, and then adding an alcohol in the presence of HF again, but can also be carried out continuously from the above carbonylation reaction by further adding HF and/or an alcohol to the above carbonylation reaction-produced liquid.

The preferred amount of HF used in the esterification reaction is the same as the one described for the carbonylation reaction, and redundant description here is omitted.

Examples of the alcohol as a secondary raw material used in the esterification reaction include the same as those described for the carbonylation reaction, that is, monohydric alcohols such as methanol, ethanol, n-propanol, iso-propanol, n-butanol, iso-butanol, and tert-butanol.

The total of the amount of the alcohol used in the esterification reaction and the amount used in the carbonylation reaction is preferably 1.0 to 2.0 times by mole based on the compound represented by formula (2), which is the main raw material, from the viewpoint of increasing the reaction efficiency to obtain the target having high purity. By setting the amount of the alcohol used in the esterification reaction within such a range, the remaining of the unreacted acyl fluoride in the reaction product is reduced, and a decrease in product purity due to the remaining of the acyl fluoride in the reaction product together with the target ester compound tends to be suppressed. On the other hand, by setting the amount of the alcohol used within such a range, the proportion of the remaining unreacted alcohol is reduced, and the separation (isolation) of the obtained target becomes easy, and therefore the product purity tends to be increased.

In addition, due to the dehydration reaction of the unreacted alcohol, water is produced as a by-product in the reaction system, and this water undergoes azeotropy with HF and therefore is accumulated in recovered HF. When the recovered HF in which this water is accumulated is reused in the reaction, the problems of adversely affecting the reaction and causing significant corrosion of the apparatus material occur. By setting the amount of the alcohol used in the above preferred range, the above problems tend to be reduced.

Here, from the viewpoint of obtaining the carboxylic acid ester compound represented by formula (1) in high yield, respective predetermined amounts of the alcohols are preferably added in both steps of the carbonylation reaction and the esterification reaction. In this case, it is more preferred that in the carbonylation reaction, the amount of the alcohol is 0.1 to 0.5 times by mole based on the compound represented by formula (2), which is the main raw material, and in the esterification reaction, the amount of the alcohol is further increased and set to be 1.0 to 2.0 times by mole, combined with the amount added during the carbonylation reaction, based on the compound represented by formula (2), which is the main raw material. From the viewpoint of efficiently isolating the obtained target, the alcohol used in the esterification reaction, and the alcohol optionally used in the carbonylation reaction are preferably the same.

(Esterification Reaction Conditions)

The reaction temperature in the above esterification reaction is not particularly limited but is preferably 20° C. or more and 10° C. or less from the viewpoint of suppressing side reactions to increase the yield, and the viewpoint of the suppression of the production of water as a by-product due to the dehydration reaction of the added alcohol. The reaction time is not particularly limited but is preferably 0.5 to 3 h from the viewpoint of allowing the esterification reaction to proceed sufficiently and increasing the efficiency. Here, the esterification reaction is preferably performed under pressurization from the viewpoint of increasing the reaction efficiency. From the viewpoint of increasing the reaction efficiency and reducing the facility burden, the pressure is preferably 0.1 to 5.0 MPa, more preferably 1.0 to 3.0 MPa. The form of the esterification reaction is not particularly limited and may be any method, for example, a batch type, a semicontinuous type, or a continuous type. The end point of the reaction is not particularly limited but should be determined with reference to the point in time when no reaction heat increase is noted.

A mixed solution (esterification reaction-produced liquid) containing the carboxylic acid ester compound represented by formula (1), HF, and a solvent, an alcohol, and the like as needed is obtained by the above-described esterification reaction. A complex of the carboxylic acid ester compound represented by formula (1) and HF can be contained in this esterification reaction-produced liquid, but, for example, by heating the esterification reaction-produced liquid to decompose the bond between the carboxylic acid ester represented by formula (1) and HF, HF can be vaporized and separated, recovered, and reused. From the viewpoint of suppressing the heat deterioration, isomerization, and/or the like of the product, this complex decomposition operation is preferably performed as quickly as possible. In order to quickly advance the thermal decomposition of the complex, for example, heating is preferably performed under reflux of a solvent inert to HF, for example, a saturated aliphatic hydrocarbon such as heptane, and/or an aromatic hydrocarbon such as benzene.

The isolation of the carboxylic acid ester compound represented by formula (1) can be performed according to an ordinary method, and its method is not particularly limited. For example, the carboxylic acid ester compound represented by formula (1) can be obtained with high purity by drawing the esterification reaction-produced liquid into ice water to separate the oil phase and the aqueous phase, then washing the oil phase alternately with a sodium hydroxide aqueous solution and distilled water, performing dehydration with anhydrous sodium sulfate, further removing the low-boiling materials and the like using an evaporator, and then, for example, performing rectification using a rectifying column having a theoretical plate number of 20 or more.

The carboxylic acid ester compound represented by formula (1) that can be obtained in this manner can be effectively used alone or in combination with other components, as a fragrance component (perfuming component) or as a formulated fragrance material, in various applications, for example, cosmetics, health and sanitary materials, daily necessities, sundry articles, fibers, fiber products, clothing, food, quasi-drugs, and medicaments.

The carboxylic acid ester compound represented by formula (1) is a novel compound having a bulky ring structure of a 7-(2,2-dimethylcyclobutyl)-5-methylbicyclo[3.2.1]octane moiety. Compounds having bulky ring structures such as norbornene and adamantane are known to be compounds useful as raw materials (including intermediates in organic synthesis) of medicaments, agricultural chemicals, functional resins, optical functional materials, electronic functional materials, and the like. In addition, the compound of this embodiment comprises an ester structure, and the desired compound can also be derived using the ester as the starting point of a reaction. Further, the carboxylic acid ester compound represented by formula (1) also has, in addition to the bulky ring structure, stiffness, light transmission properties, high Tg, lubricity (fat solubility), and the like, and using these, the carboxylic acid ester compound represented by formula (1) can also be effectively used as a raw material (including an intermediate in organic synthesis) of medicaments, agricultural chemicals, functional resins, optical functional materials such as liquid crystals and resists, electronic functional materials, and the like.

[Fragrance Composition]

The fragrance composition of this embodiment contains a carboxylic acid ester compound represented by formula (1). The fragrance composition of this embodiment may contain any other components as long as it contains the carboxylic acid ester compound represented by formula (1).

The fragrance composition of this embodiment may comprise, for example, other fragrance components (perfuming components) other than the carboxylic acid ester compound represented by formula (1), as other components.

As the above-described other fragrance components, for example, hydrocarbons, alcohols, phenols, esters, aldehydes, ketones, acetals, ketals, ethers, nitriles, lactones, hydrocarbons, musks, natural fragrances, natural essential oils or natural extracts, plant extracts, and animal fragrances having terpene skeletons or the like are known, and various ones are described, for example, in Koryo Kagaku Soran (Complete Guide to Fragrance Chemistry) 1, 2, and 3 (written by Osamu Okuda, published by Hirokawa Shoten), Gosei Koryo (Synthetic Fragrances) (written by Motoichi Indo, The Chemical Daily Co., Ltd.), and "The Japan Patent Office, Collection of Well-known Prior Arts (Koryo (Fragrances)) Part III Koshohin Koryo (Cosmetic Fragrances), P26-103, published on Jun. 15, 2001".

Specific examples of other fragrance components include, but are not particularly limited to, hydrocarbons such as limonene, α-pinene, β-pinene, terpinene, cedrene, longifolene, and valencene;

alcohols such as linalool, citronellol, geraniol, nerol, terpineol, dihydromyrcenol, ethyl linalool, farnesol, nerolidol, cis-3-hexenol, cedrol, menthol, borneol, β-phenylethyl alcohol, benzyl alcohol, phenylhexanol, 2,2,6-trimethylcyclohexyl-3-hexanol, 1-(2-t-butylcyclohexyloxy)-2-butanol, 4-isopropylcyclohexanemethanol, 4-methyl-2-(2-methylpropyl)tetrahydro-2H-pyran-4-ol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, isocamphylcyclohexanol, and 3,7-dimethyl-7-methoxyoctan-2-ol;

phenols such as eugenol, thymol, vanillin, and vanitrope;

esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate (also referred to as FLORAMAT (product name)), p-t-butylcyclohexyl acetate, tricyclodecenyl acetate, benzyl acetate, styralyl acetate, cinnamyl acetate, dimethylbenzylcarbinyl acetate, dimethylbenzylcarbinyl butyrate, 3-pentyltetrahydropyran-4-yl acetate, citronellyl propionate, tricyclodecenyl propionate, allylcyclohexyl propionate, ethyl 2-cyclohexyl propionate, benzyl propionate, benzyl butyrate, citronellyl butyrate, dimethylbenzylcarbinyl n-butyrate, tricyclodecenyl isobutyrate, methyl 2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyl dihydrojasmonate, methyl-2,4-dihydroxy-3,6-dimethyl benzoate, ethylmethylphenyl glycidate, methyl anthranilate, and FRUITATE;

aldehydes such as n-octanal, n-decanal, n-dodecanal, 2-methylundecanal, 10-undecenal, citronellal, citral, hydroxycitronellal, dimethyltetrahydrobenzaldehyde, 4(3)-(4-hydroxy-4-methylpentyl)-3-cyclohexene-1-carbaldehyde, 2-cyclohexylpropanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde;

ketones such as methylheptenone, 4-methylene-3,5,6,6-tetramethyl-2-heptanone, amylcyclopentanone, 3-methyl-2-(cis-2-penten-1-yl)-2-cyclopenten-1-one, methylcyclopentenolone, rose ketone, γ-methylionone, α-ionone, carvone, menthone, camphor, nootkatone, benzylacetone, anisylacetone, methyl β-naphthyl ketone, 2,5-dimethyl-4-hydroxy-3(2H)-furanone, maltol, ethyl maltol, 7-acetyl-1,2,3,4,5,6,7,8-octahydro-1,1,6,7-tetramethylnaphthalene, muscone, civetone, cyclopentadecanone, and cyclohexadecenone;

acetals and ketals, such as acetaldehyde ethylphenylpropyl acetal, citral diethyl acetal, phenylacetaldehyde glycerin acetal, and ethyl acetoacetate ethylene glycol ketals;

ethers such as anethole, β-naphthyl methyl ether, β-naphthyl ethyl ether, limonene oxide, rose oxide, 1,8-cineole, and racemic or optically active dodecahydro-3a,6,6,9a-tetramethylnaphtho[2,1-b]furan;

nitriles such as citronellyl nitrile;

lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; and natural essential oils or natural extracts such as orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, cypress, vetiver, patchouli, and labdanum.

One of these can be used alone, or two or more of these can be used in combination.

The fragrance composition of this embodiment may contain various types of additives (those that do not function as fragrance components) used in cosmetics, health and sanitary materials, daily necessities, sundry articles, fibers, fiber products, clothing, food, quasi-drugs, medicaments, and the like, as needed, other than the above-described other fragrance components. Specific examples of the various types of additives include, but are not particularly limited to, solvents and/or dispersion media such as dipropylene glycol, diethyl phthalate, ethylene glycol, propylene glycol, methyl myristate, and triethyl citrate, pulverulent bodies (powders), liquid fats and oils, solid fats and oils, waxes, oil-soluble components, silicones, hydrocarbons, higher fatty acids, higher alcohols, lower alcohols, polyhydric alcohols, esters, glycols, alcohol ethers, saccharides, amino acids, organic amines, polymer emulsions, pH adjusting agents, skin nutrients, vitamins, anionic surfactants such as polyoxyethylene lauryl sulfate ether, cationic surfactants, amphoteric surfactants, nonionic surfactants, ultraviolet absorbents, oil gelling agents, moisturizers, aqueous components, propellants, antioxidants, antioxidant aids, beauty components, antiseptics, water-soluble polymers, water, film-forming agents, discoloration inhibitors, aroma fixatives, thickening agents, antifoaming agents, bactericides, deodorants, dyes, pigments, pearl agents, chelating agents, and gelling agents. One of these can be used alone, or two or more of these can be used in combination.

The fragrance composition of this embodiment can be used in any form according to the properties of a component to be perfumed, and various types of additives blended as needed, and its form of use is not particularly limited. For example, the fragrance composition of this embodiment can be used in a liquid, gel-like, semisolid, jelly-like, solid, powdery, misty, aerosol-like, emulsion-like, or suspension-like form. In addition, the fragrance composition of this embodiment can also be used in the form of being sprayed, applied, adsorbed, mixed, dispersed, emulsified, kneaded, supported, infiltrated, impregnated, or the like onto or into a base material such as organic or inorganic fibers such as yarns, a woven or knitted fabric, a woven fabric, a nonwoven fabric, or paper, a resin, a clothing material, or a garment. Further, the fragrance composition of this embodiment can also be provided to a component to be perfumed, using microcapsules or the like. The scent of the carboxylic acid ester compound represented by formula (1) and the fragrance composition in this embodiment can also be scattered or diffused using a diffuser.

The content of the carboxylic acid ester compound represented by formula (1) in the fragrance composition of this embodiment can be appropriately set according to the type of the target aroma and the intensity of the aroma, the types and amounts of other fragrance components used in combination, the desired aroma persistence, the form of use, and the like, and is not particularly limited, but is preferably 0.01 to 90% by mass, more preferably 0.1 to 50% by mass, based on the total amount of the fragrance composition.

[Applications]

The carboxylic acid ester compound represented by formula (1) has a fruity, apple-like aroma with a clean feeling, has a high preference, and has excellent aroma properties. Therefore, the carboxylic acid ester compound represented by formula (1) can be used by being blended with other components as an aroma component (perfuming component), and therefore one aspect of this embodiment is a composition containing the carboxylic acid ester compound represented by formula (1). The composition of this embodiment is not particularly limited as long as it comprises the carboxylic acid ester compound represented by formula (1) and other optional components. The type of the composition is not particularly limited, and preferred examples thereof include a cosmetic composition, a food additive composition, and a cleaning composition.

The carboxylic acid ester compound represented by formula (1) can be widely used alone as an aroma component (perfuming component) of various types of products, for example, cosmetics, health and sanitary materials, daily necessities, sundry articles, fibers, fiber products, clothing, food, quasi-drugs, and medicaments, or widely used as a formulated fragrance material of the various types of products, and can also be used for improving the aroma of a material to which the carboxylic acid ester compound represented by formula (1) is to be blended.

Specific examples of the various types of products include fragrance products, basic cosmetics, finishing cosmetics, head hair cosmetics, hair cosmetics, skin cosmetics, suntan cosmetics, medicated cosmetics, soaps, body cleaning agents, bath agents, detergents, softening agents, bleaching agents, disinfectant detergents, deodorant detergents, furniture care, various types of cleaning agents, glass cleaners, furniture cleaners, floor cleaners, disinfectants, insecticides, bleaching agents, aerosol agents, deodorants, air fresheners, deodorant air fresheners, repellents, and other sundry goods.

More specific examples include perfumes, parfum, eau de parfum, eau de toilette, colognes, fragrance powders, solid perfumes, shampoos, conditioners, rinses, rinse-in-shampoos, hair tonics, hair creams, brilliantines, setting lotions, hair sticks, hair solids, hair oils, hair mousses, hair gels, hair pomades, hair liquids, hair sprays, hair colors, hair packs, hair restorers, hair dyes, lotions, milky lotions, body lotions, body powders, body soaps, hand soaps, hand creams, body creams, aroma oils, beauty essences, creams, packs, foundations, face powders, lipsticks, facial cleansing foams, facial cleansing creams, makeup removers, vanishing creams, cleansing creams, cold creams, massage creams, oil blotting paper, eye shadows, eye liners, mascaras, bases, loose face powders, pressed face powders, talcum powders, lip creams, blushers, eyebrow pencils, eye packs, nail enamels, enamel removers, toilet soaps, bath soaps, perfume soaps, transparent soaps, synthetic soaps, liquid soaps, bath salts, bath tablets, bath liquids, foam baths, bath oils, bath capsules, milk baths, bath jellies, bath cubes, antiperspirants, shaving foams, after-shaving lotions, shaving gels, hair growth lotions, permanent wave agents, medicated soaps, medicated shampoos, medicated skin cosmetics, dishwashing detergents, kitchen detergents, dish detergents, laundry detergents, clothing heavy duty detergents, clothing light duty detergents, liquid detergents, compact detergents, soap powders, softeners, furniture care, disinfectant detergents, deodorant detergents, drain cleaning agents, oxidative bleaching agents, reductive bleaching agents, optical bleaching agents, aerosol agents, solid/gel-like/liquid deodorants, solid/gel-like/liquid air fresheners, solid/gel-like/liquid deodorant air fresheners, cleansers, glass cleaners, furniture cleaners, leather cleaners, floor cleaners, house cleaners, fiber cleaning agents, leather cleaning agents, toilet cleaning agents, bathroom cleaning agents, glass cleaners, mold removers, disinfectants, insecticides, dentifrices, mouthwashes, bath agents, antiperspirant products, sunscreen creams, perm solutions, depilatories, ointments, poultices, ointment agents, patches, hair growth agents, gargles, toilet paper, tissues, scent paper, room fragrances, aroma candles, and aroma oils.

The amount used in these various types of products can be appropriately set according to the type of the target aroma and the intensity of the aroma, the types and amounts of other fragrance components used in combination, the desired aroma persistence, the form of use, the use environment, and the like, and is not particularly limited, but is preferably 0.001 to 50° by mass, more preferably 0.01 to 20% by mass, for the carboxylic acid ester compound represented by formula (1).

EXAMPLES

The present invention will be described in more detail below by giving Examples, but the present invention is not limited to these Examples. "Parts" represents "parts by mass" unless otherwise noted below.

The measurement methods in the Examples are shown below.

<Gas Chromatography Analysis Conditions>

Gas chromatography was carried out using a gas chromatograph GC-2010 manufactured by SHIMADZU CORPORATION, and ULBON HR-1 (0.32 mm φ×25 m×0.50 μm) manufactured by SHINWA CHEMICAL INDUSTRIES, LTD. as a capillary column. As the temperature increase conditions, the temperature was increased from 100° C. to 300° C. at 5° C./rain.

Detector: FID (detector temperature 310° C.)
Column: HR-1 Capillary column
Column temperature: 100° C. (temperature increase rate 5° C./min)
Carrier gas: $N_2$ (flow rate 1.8 mL/min)
Sample injection temperature: 310° C.
Amount of sample injected: 0.2 μL
Injection port temperature: 310° C.
Retention time: 0 min <Yield of Carboxylic Acid Ester Compound>

The area proportions (GC %) of a compound represented by formula (1), which was the target product, and its isomers (the compound represented by formula (1) is not included in these isomers), which were by-products, were obtained by gas chromatography analysis. A mixture of the compound represented by formula (1) and its isomers is referred to as an "isomer-containing carboxylic acid ester compound" below.

<GC-MS>

GC-MS was carried out using a GC-MS spectrum apparatus GCMS-QP2010 ULTRA manufactured by SHIMADZU CORPORATION.

<$^1$H-NMR Spectrum Analysis>

Measurement was performed using an NMR apparatus ECA-500 manufactured by JEOL Ltd. For the internal standard substance, tetramethylsilane (TMS) was used.

<Example 1> Synthesis of 7-(2,2-Dimethylcyclobutyl)-5-methylbicyclo[3.2.1]octane-1-carboxylic Acid Ethyl Ester

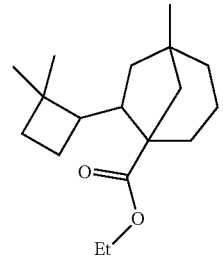

An experiment was performed using a stainless steel autoclave having an internal volume of 500 ml which was equipped with a magnetic force-induced stirring type stirrer and three inlet nozzles in the upper portion and one drawing nozzle at the bottom and whose internal temperature was adjustable by a jacket.

First, the inside of the autoclave was purged with carbon monoxide, and then 100 g (5.0 mol) of anhydrous HF was introduced into this inside of the autoclave, and the liquid temperature was set at 0° C. Then, the inside of the autoclave was pressurized to 2.0 MPa with carbon monoxide. Then, while the temperature and pressure of the inside of the autoclave were maintained at 0° C. and 2.0 MPa respectively, a mixed liquid of 102 g (0.5 mol) of β-caryophyllene represented by formula (2), 100 g of heptane, and 4.6 g (0.1 mol) of ethanol was supplied from the upper portion of the autoclave, and after the completion of the supply of the raw materials, stirring was continued for 1 h (carbonylation reaction step).

Next, following the carbonylation reaction, under the condition of 2.0 MPa, the temperature of the inside of the autoclave was decreased, and while the temperature was kept at 0° C., 23 g (0.5 mol) of ethanol was supplied from the upper portion of the autoclave, and after the completion of the supply of the raw material, stirring was continued for 1 h (esterification reaction step).

Then, the reaction-produced liquid was drawn into ice water from the bottom of the autoclave to separate the oil phase and the aqueous phase, and then the oil phase was recovered, and this oil phase was washed twice with 100 mL of a 2% by mass sodium hydroxide aqueous solution and twice with 100 mL of distilled water and further dehydrated with 10 g of anhydrous sodium sulfate. Then, a sample was taken from the finally obtained liquid, and gas chromatography was conducted using this sample. As a result, the yield of the isomer-containing carboxylic acid ester compound was 37.4% (GC area %).

In addition, as a result of analysis by GC-MS, the molecular weight of the main product was 278.4.

Further, it was confirmed by $^1$H-NMR ($^1$H-NMR spectrum data are shown in FIG. 1), $^{13}$C-NMR, HMQC, HMBC, and INADEQUAT measurement in a deuterated chloroform solvent that the main product was 7-(2,2-dimethylcyclobutyl)-5-methylbicyclo[3.2.1]octane-1-carboxylic acid ethyl ester. Also for the $^{13}$C-NMR, HMQC, HMBC, and INADEQUAT measurement, the same apparatus and sample as the $^1$H-NMR measurement were used.

In the $^1$H-NMR, the following characteristic peaks for 7-(2,2-dimethylcyclobutyl)-5-methylbicyclo[3.2.1]octane-1-carboxylic acid ethyl ester were observed.

Hydrogen of methylene of EtO group; —OCH$_2$CH$_3$: 4.11 ppm (q, J=7.5 Hz, 2H)

Hydrogen of methyl of EtO group; —OCH$_2$CH$_3$: 1.25 ppm (t, J=7.5 Hz, 3H)

Hydrogen of three methyl groups: 0.98 ppm (s, 3H), 0.96 ppm (s, 3H), 0.89 ppm (s, 3H)

The above chemical shift values are based on TMS, and s indicates that the signal is a singlet, t indicates that the signal is a triplet, and q indicates that the signal is a quartet.

In the $^{13}$C-NMR, the carbon atom of the carbonyl group of 7-(2,2-dimethylcyclobutyl)-5-methylbicyclo[3.2.1]octane-1-carboxylic acid ethyl ester was observed at 176.7 ppm.

Example 2

The carbonylation reaction step, the esterification reaction step, and the treatment of the reaction-produced liquid were performed as in Example 1 except that the carbonylation reaction step was performed at −20° C.

As a result of analyzing the obtained liquid by gas chromatography, the yield of the isomer-containing carboxylic acid ester compound was 23.8% (GC area %).

Example 3

The carbonylation reaction step, the esterification reaction step, and the treatment of the reaction-produced liquid were performed as in Example 1 except that the carbonylation reaction step was performed under carbon monoxide pressurization at 1.0 MPa.

As a result of analyzing the obtained liquid by gas chromatography, the yield of the isomer-containing carboxylic acid ester compound was 18.9% (GC area %).

The samples comprising 7-(2,2-dimethylcyclobutyl)-5-methylbicyclo[3.2.1]octane-1-carboxylic acid ethyl ester obtained in Examples 1 to 3 had a fruity, apple-like aroma with a clean feeling, had a high preference, and had excellent aroma properties.

Example 4

5 Parts by mass of the carboxylic acid ester compound obtained in Example 1 was added to 95 parts by mass of a fragrance composition having the composition shown in Table 1 to obtain the fragrance composition of Example 4. The fragrance composition having the composition shown in Table 1 is a fruit type fragrance composition, and by adding the carboxylic acid ester compound obtained in Example 1, a fresh fruity feeling was provided, and a fruit type fragrance composition having a high preference was obtained.

The evaluation of the aroma of the compounds and the fragrance composition obtained by the Examples was performed by skilled panelists in prepared fragrance evaluation business.

TABLE 1

| Blended component | Parts by mass |
| --- | --- |
| Dimethylbenzylcarbinyl butyrate | 60 |
| Dimethylbenzylcarbinyl acetate | 10 |
| Benzyl butyrate | 5 |
| FRUITATE (manufactured by Kao Corporation) | 5 |
| FLORAMAT (manufactured by Kao Corporation) | 5 |
| Benzyl alcohol | 3 |
| Ethyl maltol | 3 |
| γ-Undecalactone | 1 |
| Vanillin | 1 |
| Vanitrope | 1 |
| Rose type | 1 |
| Total | 95 |

This application is based on Japanese Patent Application No. 2018-132789 filed on Jul. 13, 2018, the contents of which are incorporated herein by reference.

INDUSTRIAL APPLICABILITY

The carboxylic acid ester compound according to the present invention has industrial applicability in the fields of medicaments, agricultural chemicals, fragrances, functional resins, optical functional materials, electronic functional materials, and the like.

The invention claimed is:

1. A carboxylic acid ester compound represented by formula (1),

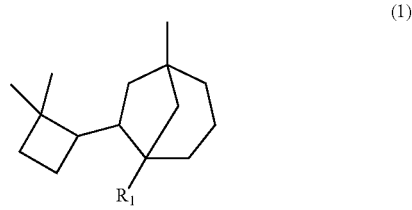

wherein $R_1$ is —COOR, wherein R is an alkyl group having 1 to 4 carbon atoms.

2. A fragrance composition comprising the carboxylic acid ester compound according to claim 1.

3. A composition comprising the carboxylic acid ester compound according to claim 1.

4. The composition according to claim 3, for use in cosmetics, food additives, or cleaning compositions.

5. A method for producing a carboxylic acid ester compound represented by formula (1), comprising a step of reacting β-caryophyllene represented by formula (2) with carbon monoxide and then a monohydric alcohol having 1 to 4 carbon atoms in the presence of hydrogen fluoride,

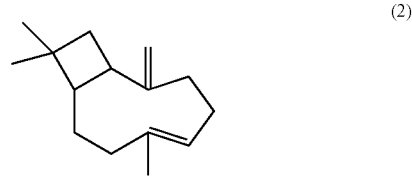

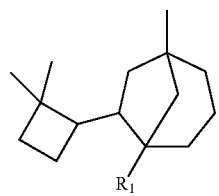
(1)
wherein $R_1$ is —COOR, wherein R is an alkyl group having 1 to 4 carbon atoms.
* * * * *